US007363881B2

(12) United States Patent
Gorans et al.

(10) Patent No.: US 7,363,881 B2
(45) Date of Patent: Apr. 29, 2008

(54) BEAK TREATMENT WITH TONGUE PROTECTION

(75) Inventors: Marc S. Gorans, Willmar, MN (US); Scott C. Johnson, Blomkest, MN (US)

(73) Assignee: Nova-Tech Engineering, Inc., Willmar, MN (US)

( * ) Notice: Subject to any disclaimer, the term of this patent is extended or adjusted under 35 U.S.C. 154(b) by 0 days.

(21) Appl. No.: 10/702,369

(22) Filed: Nov. 6, 2003

(65) Prior Publication Data

US 2005/0115521 A1 Jun. 2, 2005

(51) Int. Cl.
*A01K 15/04* (2006.01)
*A61B 18/04* (2006.01)

(52) U.S. Cl. ...................................... 119/837; 606/164

(58) Field of Classification Search ................ 606/164, 606/104; 119/839, 837
See application file for complete search history.

(56) References Cited

U.S. PATENT DOCUMENTS 2,448,421 A 8/1948 Davis
2,484,088 A 10/1949 Hayes
2,501,283 A 3/1950 McKnight
2,505,559 A 4/1950 Lyon
2,713,325 A 7/1955 Bowers
2,731,016 A 1/1956 Miller
2,742,904 A 4/1956 Lyon
2,792,004 A 5/1957 Sandy
2,952,031 A 9/1960 Breitkreutz
3,136,315 A 6/1964 Lyon
3,274,974 A 9/1966 Reynolds
3,295,524 A 1/1967 Parker
3,302,645 A 2/1967 Lockmiller
3,390,679 A * 7/1968 Turner ........................ 606/163
3,502,079 A 3/1970 Simmons
3,570,487 A 3/1971 Reynolds
3,593,714 A 7/1971 Lyon
3,623,186 A 11/1971 Panek
3,812,857 A * 5/1974 Lyon .......................... 606/163
3,964,481 A 6/1976 Gourlandt et al.
3,994,292 A 11/1976 Goodwin
4,019,513 A 4/1977 Kaniecki
4,026,289 A 5/1977 Hendrix
4,040,425 A 8/1977 Goodling et al.
4,191,130 A 3/1980 Musgrave
4,343,310 A 8/1982 DuBose et al.
4,375,814 A 3/1983 Gourlandt
RE31,202 E 4/1983 Goodling et al.
4,446,819 A * 5/1984 Gourlandt .................. 119/714
4,681,565 A 7/1987 Gourlandt
4,951,610 A 8/1990 Gourlandt
5,195,925 A 3/1993 Gorans et al.
5,651,731 A * 7/1997 Gorans et al. .............. 606/164
2004/0143278 A1* 7/2004 Gorans et al. .............. 606/164

FOREIGN PATENT DOCUMENTS

NL 8 802 812 6/1990
NL 8802812 A * 6/1990

* cited by examiner

*Primary Examiner*—Andrea M. Valenti
(74) *Attorney, Agent, or Firm*—Mueting, Raasch & Gebhardt, P.A.

(57) ABSTRACT

The present invention provides apparatus and methods for treating the beaks of poultry to prevent further growth by non-contact heating while protecting the birds' tongues. The birds' tongues are protected by providing pressure on underside of the lower beak of the bird, proximate the base of the lower beak.

24 Claims, 2 Drawing Sheets

BEAK TREATMENT WITH TONGUE PROTECTION

BACKGROUND

The beak of a bird is a weapon and a tool for eating. In commercial production, poultry are raised in close proximity to each other. In this environment, young birds may use their beaks for pecking other birds, potentially causing disfigurement, illness, or death. The sharp tip of the beak is the most dangerous part of the beak. In addition, adult poultry may use their beaks as weapons to damage other adult and juvenile poultry. This use of the beak as a weapon causes economic losses for the poultry producer. Accordingly, a portion of the beak is typically removed from poultry to minimize its effectiveness as a weapon.

Previously, debeaking methods were based on the principle of killing all tissue just ahead of the nostril by severing the blood supply and generally destroying the tissue of the beak. This was done through cutting the beak with a blade or by bringing the beak in contact with a hot object to burn through the beak. Although bleeding may be minimized by cauterization, the wound resulting from these processes produced a substantial amount of pain and shock in the bird.

In these prior art processes, imprecise positioning of the beak and ineffectiveness of the method used resulted in several disadvantages. For example, the beak could heal and regenerate if the blood supply to the beak was not completely cut. Furthermore, when the veins are cut close to the nostril, they are large and difficult to seal resulting in problems avoiding infection or bleeding. The prior art method also could induce severe shock and pain to the bird.

U.S. Pat. No. 5,651,731 (Gorans et al.) addresses many of these issues. For example, the apparatus and methods described therein provide a more humane method for treating the beaks of poultry because the method is bloodless, induces little or no shock, and minimizes damage to the bird. It did not, however, address the issue of retardation in growth of the lower beak of a bird. In fact, the method and apparatus were specifically designed to avoid treating the lower beak of the bird. Allowing the lower beak to grow without interference may, however, allow some species of birds (e.g., chickens) to scatter significant amounts of food using that lower beak. The scattered food is typically wasted and does not contribute to the nutrition of the bird.

Another issue that may be raised by treating only the upper beak of a bird is that mating behavior may be adversely affected. In some species of birds, e.g., chickens, the male bird typically grasps the female in his beak during mating. If the male's lower beak extends past the upper beak, the male's ability to grasp the female may be inhibited, thereby adversely affecting mating behavior and/or success.

Previous attempts by the inventors to provide methods and apparatus for treating the lower beak may, however, inadvertently damage the tongue of the bird if the bird's tongue is extended into the beak during the beak treatment process. Birds with damaged tongues may experience difficulties in eating, thereby reducing the growth rate of the bird.

SUMMARY OF THE INVENTION

The present invention provides apparatus and methods for treating the beaks of poultry to prevent further growth by non contact heating while protecting the birds' tongues. Although it may be desirable that some species of birds retain their lower beaks without any change after beak treatment, it may be more desirable to retard the growth of the lower beak in other species (e.g., chickens). In any event, it is almost always desirable to protect the birds' tongues during any beak treatment process (irregardless of whether the bird's upper and/or lower beaks are being treated).

The beak treatment process involves the delivery of energy to the beak or beaks in amounts sufficient to retard the growth and/or result in erosion of portions of the treated beaks. The energy incident on one of the upper beak or lower beak may be reflected from an energy director (e.g., a reflector) or it may be provided by a separate energy source as described in, e.g., U.S. patent application Ser. No. 10/346,981, titled APPARATUS AND METHOD FOR UPPER AND LOWER BEAK TREATMENT, filed Jan. 17, 2003.

Because the rate at which energy is delivered and/or the energy density of the energy delivered while treating beaks may be significant, protection of the birds' tongues may be desired when treating their beak or beaks by the delivery of energy. The present invention provides methods and apparatus for protecting the birds' tongues by pressing inward on the throat of the bird proximate the base of lower beak. Such pressure will typically cause the birds to retract their tongues from the beaks and/or prevent the birds from extending their tongues into the beak. These actions typically and preferably do not cause any long-term significant damage to the birds' tongues and/or throat that would impair their ability to eat.

Advantages of the present invention may include the ability to treat lower beak of a bird with energy that is delivered at a rate and/or density that is higher than would otherwise be safely used if the location of the birds' tongues were not controlled. In other words, without the methods and apparatus of the present invention, the delivery rate and/or density levels may need to be limited to reduce the likelihood that the birds' tongues will be damaged if they are extended into the beak during the treatment process.

When using the methods and apparatus of the present invention, however, the locations of the birds' tongues can be controlled to prevent the birds from extending their tongues into the beak during beak treatment. As a result, higher delivery rates and/or energy density can be used with a reduced chance of inadvertently damaging the birds' tongues.

A potential advantage of using higher energy delivery rates and/or energy density is that the repeatability of the beak treatment process may be improved because the total amount of energy delivered may be increased as compared to processes in which damage to the birds' tongues was a limiting factor. Alternatively, the higher rate of energy delivery and/or energy density alone may improve repeatability (even if the total amount of energy delivered were the same). In other words, the repeatability of the beak treatment process may be at least partially dependent on the energy delivery rate and/or the density of the energy delivered during treatment.

Another potential advantage of using higher energy delivery rates and/or energy density is that the time required to treat the birds' beaks may be reduced as compared to beak treatment processes in which the energy is delivered at a lower rate and/or density. Reduced treatment time may result in a corresponding reduction in any discomfort that may be experienced by the birds during the treatment process.

In one aspect, the present invention provides a method of treating the lower beak of a bird by positioning a bird head in a bird head positioning device, wherein the bird head positioning device has first and second major sides, and a beak receiving aperture formed through the first and second major sides of the bird head positioning device, wherein at least a portion of the lower beak of the bird head protrudes through the beak receiving aperture and is exposed proximate the second major side of the bird head positioning device; pressing inward on the throat of the bird proximate the base of the lower beak, wherein the pressing is directed towards the tongue of the bird; emitting energy from a non-contact energy source; and directing the energy emitted from the non-contact energy source at the second major surface of the bird head positioning device, wherein the energy is incident on the lower beak exposed proximate the second major side of the bird head positioning device while pressing inward on the throat of the bird.

In another aspect, the present invention provides an apparatus for treating the lower beak of a bird, the apparatus including a bird head positioning device having first and second major sides and a beak receiving aperture formed through the first and second major sides, the bird head positioning device adapted to position the head of a bird proximate the first major side, wherein at least a portion of the beak of the bird head protrudes through the beak receiving aperture and is exposed proximate the second major side of the bird head positioning device; a non-contact energy source emitting energy; an energy director directing energy from the non-contact energy source, wherein energy emitted from the non-contact energy source is incident on at least a portion of the lower beak exposed proximate the second major side of the bird head positioning device; and a tongue control protrusion located proximate the bird head positioning device, wherein the tongue control protrusion presses into the throat of the bird proximate the lower beak when the lower beak of the bird head protrudes through the beak receiving aperture.

In another aspect, the present invention provides an apparatus for treating the beak of a bird, the apparatus including a bird head positioning device adapted to position the head of a bird such that at least a portion of the beak of the bird protrudes from a beak receiving aperture of the bird head positioning device; a non-contact energy source emitting energy; an energy director directing energy from the non-contact energy source at the portion of the beak protruding from the beak receiving aperture; and a tongue control protrusion extending into the beak receiving aperture, wherein the tongue control protrusion is located within the beak receiving aperture such that the tongue control protrusion presses into the throat of the bird proximate a lower beak of the bird.

These and other features and advantages of the invention may be described in more detail below with respect to illustrative embodiments of the invention.

DETAILED DESCRIPTION OF ILLUSTRATIVE EMBODIMENTS OF THE INVENTION

In the following detailed description of illustrative embodiments, reference is made to the accompanying drawings that form a part hereof, and in which are shown, by way of illustration, specific embodiments in which the invention may be practiced. It is to be understood that other embodiments may be utilized and structural changes may be made without departing from the scope of the present invention. Furthermore, like reference numbers denote like features in the different figures.

The methods and apparatus of the present invention can be used in any suitable system in which the upper and/or lower beaks of live poultry are treated to retard and/or prevent growth of the beaks. Various beak treatment systems may be described in, e.g., U.S. Pat. No. 5,651,731 (Gorans et at.) and U.S. patent application Ser. No. 10/346,981, titled APPARATUS AND METHOD FOR UPPER AND LOWER BEAK TREATMENT, filed Jan. 17, 2003.

Figure 1:
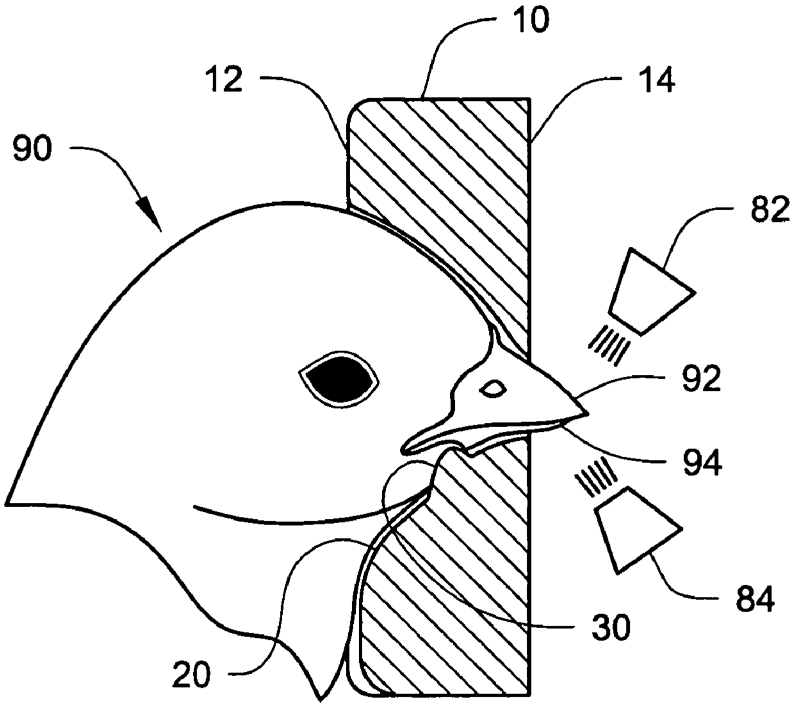
FIG. 1 is a cross-sectional view of one bird head positioning device according to the present invention with a bird head located therein.
Figure 2:
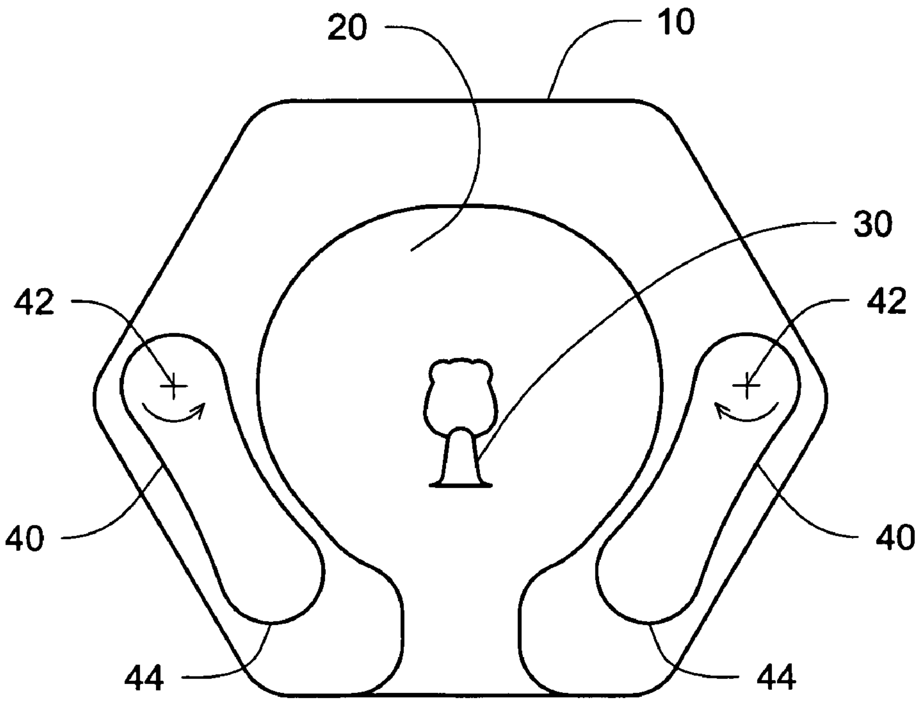
FIG. 2 is plan view of the first major side of the positioning device of FIG. 1 with the bird's head removed.

Referring to FIGS. 1 & 2, the apparatus of the present invention includes a head positioning device 10 with a first major side 12 and a second major side 14. A beak receiving aperture 20 is formed through the first and second major sides 12 and 14. The beak receiving aperture 20 may preferably be sized and shaped to receive a portion of the bird's head 90 as shown in FIG. 1 to facilitate retention of the bird's head and accurate positioning of both the upper beak 92 and the lower beak 94 within the beak receiving aperture 20.

When a bird head 90 is positioned in the beak receiving aperture as depicted in FIG. 1, at least a portion of the upper beak 92 and/or lower beak 94 is/are exposed proximate the second major side 14 of the head positioning device 10. It may be preferred that a portion of the upper beak 92 and a portion of the lower beak 94 be exposed such that both the upper beak 92 and the lower beak 94 can be treated at the same time. In some instances, however, only the upper beak 92 or the lower beak 94 may be exposed at any given time.

Also depicted in FIG. 1 are non-contact energy emitters 82 and 84 that preferably deliver energy to the upper beak 92 and the lower beak 94 in amounts sufficient to retard or prevent the growth of the beaks. The non contact energy emitters 82 and 84 are preferably operably connected to a "non-contact energy source" that is capable of heating the beak of a live bird without physical contact of a solid object such as a heated wire, heated blade, etc. Examples of suitable non-contact energy sources include, but are not limited to, lasers, bulbs emitting infrared radiation, heated fluids, etc.

Although two energy emitters 82 and 84 are depicted in FIG. 1, they may be connected to a common non-contact energy source or they may each be powered by a separate non-contact energy source. In another alternative, the energy emitter 84 delivering energy to the lower beak 94 may be a reflector or other energy director as described in, e.g., U.S. patent application Ser. No. 10/346,981, titled APPARATUS AND METHOD FOR UPPER AND LOWER BEAK TREATMENT, filed Jan. 17, 2003.

The energy emitters 82 and 84 may radiate electromagnetic energy, where "electromagnetic energy" includes energy with wavelengths/frequencies suitable for delivering sufficient energy by radiation to the beak of a bird to effect thermal beak treatment as discussed herein. As such, it may be preferred that the electromagnetic energy be within the visible spectrum, the infrared spectrum, or a combination of the visible and infrared spectrums (although electromagnetic energy outside of those spectrums may be used if sufficient energy can be delivered to the beak via radiation to accomplish thermal beak treatment).

Alternatively, the energy emitters may deliver energy to the beak or beaks by convection. Regardless of the type of energy or its delivery mechanism, the energy should penetrate through the outer layers of the beak to the inner layers, killing a portion of the beak tissue thus exposed to the radiated electromagnetic energy and destroying the ability of the soft tissues of the inner beak to develop into hard tissue.

The head positioning device 10 includes a tongue control protrusion 30 located within the beak receiving aperture 20. The tongue control protrusion 30 is positioned such that, when a bird head 90 is positioned in the beak receiving aperture 20 as depicted, the tongue control protrusion 30 presses inward on the throat of the bird 90 proximate the base of the lower beak 94. Pressing inward on the throat of the bird in that location protects the tongue of the bird 90 during a beak treatment process in which energy is directed at the upper and/or lower beaks 92 and 94 of the bird.

The tongue is protected because, if the bird's tongue is extended towards the tip of the beak, the pressure provided by the tongue control protrusion 30 causes the bird 90 to withdraw its tongue away from the tip of the beak. If the bird's tongue is already retracted (i.e., withdrawn from the tip of the beak) when the bird's head 90 is positioned within the beak receiving aperture 20, the pressure provided by the tongue control protrusion 30 preferably prevents or at least restricts the bird from extending its tongue towards the tip of the beak.

The exact position of the tongue control protrusion 30, its precise shape and other variables are dependent on a variety of factors such as the type of poultry to be treated (e.g., chickens, turkeys, ducks, etc.), the age of the poultry (older birds will typically be larger), etc. It may be preferred that the tongue control protrusion 30 does not deform the throat of the bird such that its respiration is adversely impaired during the beak treatment process.

Another feature of the tongue control protrusion 30 that may be adjusted based on the factors listed above is the distance by which the tongue control protrusion 30 extends into the beak receiving aperture 20. Again, the distance by which the tongue control protrusion 30 extends into the beak receiving aperture 20 is dependent on a variety of factors such as the type of poultry to be treated (e.g., chickens, turkeys, ducks, etc.), the age of the poultry (older birds will typically be larger), etc.

Referring to FIG. 2 (a plan view of the first major side 12 of the head positioning device 10), a pair of retaining arms 40 are preferably provided on the head positioning device 10 to retain the bird's head within the beak receiving aperture 20. It may be preferred that the retaining arms 40 rotate about points 42 (in the plane of the paper on which FIG. 2 is located). When rotated inward as indicated by the arrows proximate points 42, the ends 44 of the retaining arms 40 are located behind the bird's neck, preventing the bird from removing its head 90 from the beak receiving aperture 20. The retaining arms 40 preferably urge the bird's head 90 into position within the beak receiving aperture 20, such that the tongue control protrusion 30 can apply the desired pressure to the bird as discussed herein. Similar retaining arms are depicted in, e.g., U.S. Pat. No. 5,651,731 (Gorans et al.) and U.S. patent application Ser. No. 10/346,981, titled APPARATUS AND METHOD FOR UPPER AND LOWER BEAK TREATMENT, filed Jan. 17, 2003.

The tongue control protrusion 30 of FIGS. 1 & 2 is an example of a fixed tongue control protrusion, i.e., the tongue control protrusion 30 is fixed within the beak receiving aperture 20. For example, the tongue control protrusion 30 may be molded into the head positioning device 10 if the head positioning device 10 is manufactured of a moldable material (e.g., plastic, etc.). Alternatively, if the head positioning device 10 is, for example, machined from metal, the tongue control protrusion 30 may be formed in the head positioning device 10 as machined. In another alternative, the tongue control protrusion 30 may be attached to a head positioning device 10 after the head positioning device 10 is formed. In that example, the tongue control protrusion 30 may be attached by adhesives, mechanical connectors, etc.

The tongue control protrusion 30 may be made of rigid materials or it may be made of, e.g., silicone or some other suitable material or materials that exhibit resiliency and may elastically deform in response to an applied force. In another alternative, the tongue control protrusion 30 may be made of a combination of rigid and resilient materials (e.g., a rigid core coated with a resilient material).

Figure 3:
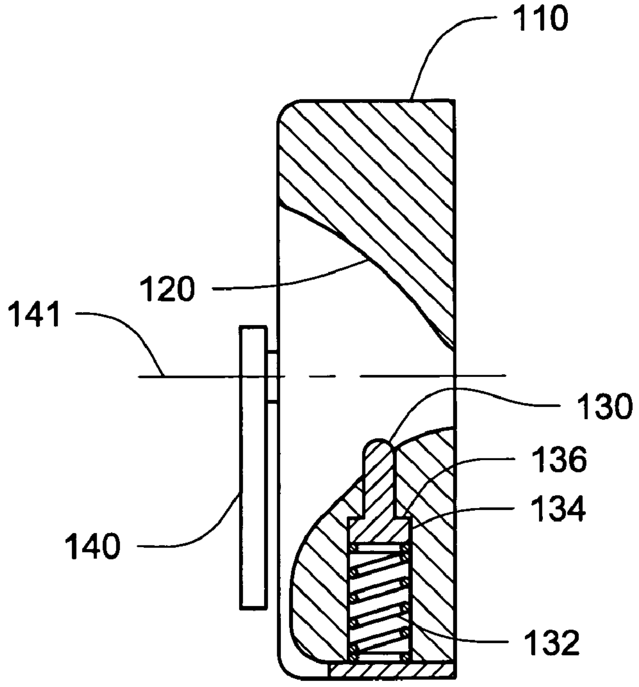
FIG. 3 is a cross-sectional view of an alternative bird head positioning device.

FIG. 3 is a cross-sectional view of an alternative head positioning device 110 that is, in many respects, similar to the head positioning device 10 of FIGS. 1 & 2. The primary difference is, however, that the tongue control protrusion 130 is not fixed within the beak receiving aperture 120. As seen in FIG. 3, the tongue control protrusion 130 is biased upwards into the beak receiving aperture 120 by a resilient member 132. The resilient member 132 may be any resilient, compressible article such as, e.g., a coil spring, elastomeric plug/bushing, leaf spring, etc. The travel of the tongue control protrusion 130 into the beak receiving aperture 120 is limited by the flange 134 that rests against shoulder 136 in the passageway in which the tongue control protrusion 130 travels.

Because the tongue control protrusion 130 is biased into the beak receiving aperture 120 by resilient member 132, the tongue control protrusion 130 may move downward (towards the resilient member 132) while a bird is being inserted into the beak receiving aperture 120. After the bird is located within the beak receiving aperture 120, the tongue control protrusion 130 may move upwards (into the beak receiving aperture 120) when the bird is in position within the beak receiving aperture 120. By moving upwards, the tongue control protrusion 130 provides the desired pressure on the bird to control movement of the bird's tongue.

The use of a resilient member 132 to bias the tongue control protrusion 130 into the beak receiving aperture 120 also provides the ability to adjust the force that the tongue control protrusion 130 can deliver to the bird. For example, the spring constant of the resilient member 132 may be selected to increase or decrease the force or pressure that the tongue control protrusion 130 delivers to the bird. As a result, the force that may be applied to a bird by the tongue control protrusion 130 may be limited by the deflection caused in the resilient member 132.

Also depicted in FIG. 3 is a retaining arm 140 mounted for rotation about axis 141 to retain a bird's head within the beak receiving aperture 120.

Figure 4:
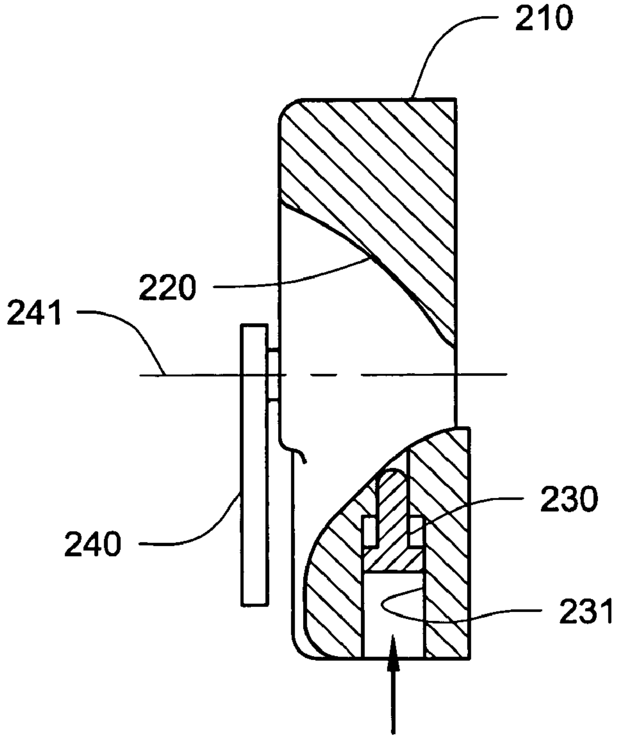
FIG. 4 is a cross-sectional view of another alternative bird head positioning device.

FIG. 4 depicts another alternative mechanism in which the tongue control protrusion 230 is not fixed within the beak receiving aperture 220 of head positioning device 210. The tongue control protrusion 230 is mounted such that it can move within the bore 231. The tongue control protrusion 230 may be moved directly by a motive force developed using pressurized fluids (with appropriate seals), electromagnetically, mechanically (using, e.g., a screw drive, rack and pinion, etc.). In another alternative, the tongue control protrusion 230 may be moved by a piston provided within bore 231 to force the tongue control protrusion 230 upwards into the beak receiving aperture 220.

In an apparatus in which the tongue control protrusion 230 can be moved, it may be preferable to withdraw the tongue control protrusion 230 from the beak receiving aperture 220 to facilitate positioning of the bird's head in the beak receiving aperture 220. After the bird's head is in position within the beak receiving aperture 220, the tongue control protrusion 230 may be moved back into the beak receiving aperture 220 where it can apply pressure as desired to the bird to control the bird's tongue during the beak treatment process. After the beak treatment process is complete, it may be desirable to again withdraw the tongue control protrusion 230 from the beak receiving aperture 220. Withdrawing the tongue control protrusion 230 may increase the comfort of the bird and/or facilitate removal of the bird's head from the beak receiving aperture.

Also depicted in FIG. 4 is a retaining arm 240 mounted for rotation about axis 241 to retain a bird's head within the beak receiving aperture 220.

In either of the embodiments depicted in FIGS. 3 & 4, the tongue control protrusion 130/230 may be manufactured of rigid materials, resilient compressible materials (e.g., elastomeric material such as, e.g., silicone, rubber, etc.), or combinations of rigid and resilient, compressible materials.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments set forth herein and that such embodiments are presented by way of example only, with the scope of the invention intended to be limited only by the claims.

The invention claimed is:

1. A method of treating the lower beak of a bird, the method comprising:

positioning a bird head in a bird head positioning device, wherein the bird head positioning device comprises first and second major sides, and a beak receiving aperture formed though the first and second major sides of the bird head positioning device, wherein at least a portion of the lower beak of the bird head protrudes through the beak receiving aperture and is exposed proximate the second major side of the bird head positioning device;

pressing inward on the throat of the bird proximate the base of the lower beak using a tongue control protrusion protruding from a surface defining the beak receiving aperture in the bird head positioning device, wherein the pressing is directed towards the tongue of the bird;

emitting energy from a non-contact energy source; and directing the energy emitted from the non-contact energy source at the second major surface of the bird bead positioning device, wherein the energy is incident on the lower beak exposed proximate the second major side of the bird head positioning device while pressing inward on the throat of the bird.

2. A method according to claim 1, wherein the pressing is performed while the bird head is positioned in the bird head positioning device.

3. A method according to claim 1, wherein the pressing is performed after the bird head is positioned in the bird head positioning device.

4. A method according to claim 1, further comprising adjusting a force used to perform the pressing.

5. A method according to claim 1, further comprising limiting a force used to perform the pressing.

6. A method according to claim 1, wherein the tongue control protrusion extends into the beak receiving aperture.

7. A method according to claim 6, further comprising adjusting a distance by which the tongue control protrusion extends into the beak receiving aperture.

8. A method according to claim 6, wherein the tongue control protrusion extends into the beak receiving aperture by a fixed distance.

9. A method according to claim 1, wherein the surface defining the beak receiving aperture extends between the first and second major sides of the bird head positioning device.

10. A method according to claim 1, wherein:

the beak receiving aperture formed through the first and second major sides of the bird head positioning device comprises a first opening in the first major side of the bird head positioning device and a second opening in the second major side of the bird head positioning device; and wherein the surface defining the beak receiving aperture extends from the first opening in the first major side to the second opening in the second major side of the bird head positioning device, wherein the surface faces the beak receiving aperture and extends around a perimeter of the beak receiving aperture between the first major side and the second major side, and wherein the lower beak of the bird head protrudes through the second opening in the second major side of the bird head positioning device;

and wherein the tongue control protrusion pressing inward on the throat of the bird proximate the base of the lower beak is a fixed tongue control protrusion that protrudes into the beak receiving aperture directly from the surface that defines the beak receiving aperture in the bird head positioning device, and wherein the position of the tongue control protrusion is fixed such that the tongue control protrusion remains stationary relative to the surface that defines the beak receiving aperture.

11. An apparatus for treating the lower beak of a bird, the apparatus comprising:

a bird head positioning device comprising first and second major sides and a beak receiving aperture formed through the first and second major sides, the bird head positioning device adapted to position the head of a bird proximate the first major side, wherein at least a portion of the lower beak of the bird head protrudes through the beak receiving aperture and is exposed proximate the second major side of the bird head positioning device;

a non-contact energy source emitting energy;

an energy director directing energy from the non-contact energy source, wherein energy emitted from the non-contact energy source is incident on at least a portion of the lower beak exposed proximate the second major side of the bird head positioning device; and a tongue control protrusion protruding from a surface defining the beak receiving aperture in the bird head positioning device, wherein the tongue control protrusion presses into the throat of the bird proximate the lower beak when the lower beak of the bird head protrudes through the beak receiving aperture.

12. An apparatus according to claim 11, wherein the tongue control protrusion is fixedly mounted relative to the beak receiving aperture of the bird head positioning device.

13. An apparatus according to claim 11, wherein the tongue control protrusion is movably mounted relative to the bird bead positioning device, wherein the position of the tongue control protrusion relative to the beak receiving aperture is adjustable when the lower beak of the bird head protrudes through the beak receiving aperture.

14. An apparatus according to claim 11, further comprising a resilient member biasing the tongue control protrusion into a position in which the tongue control protrusion presses into the throat of the bird proximate the lower beak when the lower beak of the bird head protrudes through the beak receiving aperture.

15. An apparatus according to claim 11, wherein the surface defining the beak receiving aperture extends between the first and second major sides of the bird head positioning device.

16. An apparatus according to claim 11, wherein:

the beak receiving aperture formed through the first and second major sides of the bird head positioning device comprises a first opening in the first major side of the bird head positioning device and a second opening in the second major side of the bird head positioning device; and wherein the surface defining the beak receiving aperture extends from the first opening in the first major side to the second opening in the second major side of the bird head positioning device, wherein the surface faces the beak receiving aperture and extends around a perimeter of the beak receiving aperture between the first major side and the second major side, and wherein the lower beak of the bird head protrudes through the second opening in the second major side of the bird head positioning device;

and wherein the tongue control protrusion is a fixed tongue control protrusion that protrudes into the beak receiving aperture directly from the surface that defines the beak receiving aperture in the bird head positioning device, wherein the position of the fixed tongue control protrusion is fixed such that the tongue control protrusion remains stationary relative to the surface that defines the beak receiving aperture.

17. An apparatus for treating the beak of a bird, the apparatus comprising:

a bird head positioning device adapted to position the head of a bird such that at least a portion of the beak of the bird protrudes from a beak receiving aperture of the bird head positioning device;

a non-contact energy source emitting energy;

an energy director directing energy from the non-contact energy source at the portion of the beak protruding from the beak receiving aperture; and a tongue control protrusion protruding from a surface defining the beak receiving aperture, wherein the tongue control protrusion is located within the beak receiving aperture such that the tongue control protrusion presses into the throat of the bird proximate a lower beak of the bird.

18. An apparatus according to claim 17, wherein the tongue control protrusion is fixedly mounted within the beak receiving aperture.

19. An apparatus according to claim 18, wherein the tongue control protrusion is movably mounted within the beak receiving aperture, wherein a distance by which the tongue control protrusion extends into the beak receiving aperture is adjustable.

20. An apparatus according to claim 17, further comprising a resilient member biasing the tongue control protrusion into the beak receiving aperture.

21. An apparatus for treating the lower beak of a bird, the apparatus comprising:

a bird head positioning device comprising first and second major sides and a beak receiving aperture formed through the fist and second major sides, the bird head positioning device adapted to position the head of a bird proximate the first major side, wherein at least a portion of the lower beak of the bird head protrudes through the beak receiving aperture and is exposed proximate the second major side of the bird head positioning device;

a non-contact energy source emitting energy;

an energy director directing energy from the non-contact energy source, wherein energy emitted from the non-contact energy source is incident on at least a portion of the lower beak exposed proximate the second major side of the bird head positioning device;

a tongue control protrusion protruding from a surface of the beak receiving aperture, wherein the tongue control protrusion presses into the throat of the bird proximate the lower beak when the lower beak of the bird head protrudes through the beak receiving aperture; and a resilient member biasing the tongue control protrusion into a position in which the tongue control protrusion presses into the throat of the bird.

22. An apparatus for treating the beak of a bird, the apparatus comprising:

a bird head positioning device adapted to position the head of a bird such that at least a portion of the beak of the bird protrudes from a beak receiving aperture of the bird head positioning device;

a non-contact energy source emitting energy;

an energy director directing energy from the non-contact energy source at the portion of the beak protruding from the beak receiving aperture;

a tongue control protrusion protruding from a surface of the beak receiving aperture and extending into the beak receiving aperture, wherein the tongue control protrusion is located within the beak receiving aperture such that the tongue control protrusion presses into the throat of the bird proximate a lower beak of the bird; and a resilient member biasing the tongue control protrusion into the beak receiving aperture.

23. A method of treating the lower beak of a bird, the method comprising:

positioning a bird head in a bird head positioning device, wherein the bird head positioning device comprises first and second major sides, and a beak receiving aperture formed through the first and second major sides of the bird head positioning device, wherein at least a portion of the lower beak of the bird head protrudes through the beak receiving aperture and is exposed proximate the second major side of the bird head positioning device;

pressing inward on the throat of the bird proximate the base of the lower beak using a fixed tongue control protrusion protruding directly from a surface defining the beak receiving aperture in the bird head positioning device, wherein the position of the tongue control protrusion is fixed such that the tongue control protrusion remains stationary relative to the beak receiving aperture;

emitting energy from a non-contact energy source; and directing the energy emitted from the non-contact energy source at the second major surface of the bird head positioning device, wherein the energy is incident on the lower beak exposed proximate the second major side of the bird head positioning device while the tongue control protrusion presses inward on the throat of the bird.

24. An apparatus for treating the lower beak of a bird, the apparatus comprising:

a bird head positioning device comprising first and second major sides and a beak receiving aperture formed through the first and second major sides, the bird head positioning device adapted to position the head of a bird proximate the first major side, wherein at least a portion of the lower beak of the bird head protrudes through the beak receiving aperture and is exposed proximate the second major side of the bird head positioning device;

a non-contact energy source emitting energy;

an energy director directing energy from the non-contact energy source, wherein energy emitted from the non-contact energy source is incident on at least a portion of the lower beak exposed proximate the second major side of the bird head positioning device; and a tongue control protrusion protruding directly from a surface defining the beak receiving aperture in the bird head positioning device, wherein the tongue control protrusion presses into the throat of the bird proximate the lower beak when the lower beak of the bird head protrudes through the beak receiving aperture.

* * * * *

UNITED STATES PATENT AND TRADEMARK OFFICE

CERTIFICATE OF CORRECTION

PATENT NO. : 7,363,881 B2
APPLICATION NO. : 10/702369
DATED : April 29, 2008
INVENTOR(S) : Gorans et al.

It is certified that error appears in the above-identified patent and that said Letters Patent is hereby corrected as shown below:

In column 5, at line 60, please insert the following sentence at the end of the paragraph:
--In those documents, the retaining arms 40 of the present invention are referred to as "skin bunchers."--

Signed and Sealed this

Twenty-sixth Day of August, 2008

JON W. DUDAS
*Director of the United States Patent and Trademark Office*